(12) United States Patent
Huang

(10) Patent No.: US 8,198,408 B2
(45) Date of Patent: Jun. 12, 2012

(54) METHOD FOR PREPARING POROUS COLLAGEN MATRICES

(75) Inventor: Lynn L. H. Huang, Yongkang (TW)

(73) Assignees: National Cheng Kung University, Tainan (TW); Life Fusion, LLC., Fremont, CA (US)

( * ) Notice: Subject to any disclaimer, the term of this patent is extended or adjusted under 35 U.S.C. 154(b) by 123 days.

(21) Appl. No.: 12/509,733

(22) Filed: Jul. 27, 2009

(65) Prior Publication Data

US 2011/0021753 A1    Jan. 27, 2011

(51) Int. Cl.
*A61K 38/17* (2006.01)
(52) U.S. Cl. .................................................. 530/356
(58) Field of Classification Search ................ None
See application file for complete search history.

(56) References Cited

U.S. PATENT DOCUMENTS

| | | |
|---|---|---|
| 3,368,911 A | 2/1968 | Kuntz et al. |
| 3,991,184 A | 11/1976 | Kludas et al. |
| 4,320,201 A | 3/1982 | Berg et al. |
| 4,626,286 A | 12/1986 | Lubbs |
| 4,837,285 A | 6/1989 | Berg et al. |
| 5,374,539 A | 12/1994 | Nimni et al. |
| 5,993,844 A | 11/1999 | Abraham et al. |
| 7,498,412 B2 | 3/2009 | Huang et al. |
| 2006/0235205 A1 | 10/2006 | Huang et al. |
| 2008/0268052 A1 | 10/2008 | Voytik-Harbin et al. |

FOREIGN PATENT DOCUMENTS

| | | | |
|---|---|---|---|
| JP | 2006-28138 | | 2/2006 |
| JP | 2006028138 | | 2/2006 |
| JP | 2007-211183 A | * | 8/2007 |

OTHER PUBLICATIONS

Li et al. "Ultrasonic irradiation in the enzymatic extraction of collagen", Ultrasonics Sonochemistry, 2009, 16:605-609—published on-line Feb. 2009.*
1M Acetic Acid pH calculator—< www.webqc.org/phsolver.php > Jul. 2011.*
0.5M Acetic Acid pH calculator—< www.webqc.org/phsolver.php > Jul. 2011.*
0.2M Acetic Acid pH calculator—< www.webqc.org/phsolver.php > Jul. 2011.*
0.1M Acetic Acid pH calculator—< www.webqc.org/phsolver.php > Jul. 2011.*
Gao et al. "Fabrication of Porous Collagen/Chitosan Scaffolds with Controlling Microstructure for Dermal Equivalent", Polymers for Advanced Technologies, 2003, 14:373-379).*
Machine Translation of Izume et al. JP 2007-211183A (Aug. 2007)—translated Jul. 28, 2011.*
pH of 0.03M citric acid < www.sensorex.com/support/more/ph_calculator > from Jul. 2011.*

* cited by examiner

*Primary Examiner* — Suzanne M Noakes
(74) *Attorney, Agent, or Firm* — Frenkel & Associates, PC

(57) ABSTRACT

A method of preparing porous collagen matrices directly from connective tissues using an acidic solution substantially free of salt.

16 Claims, 2 Drawing Sheets

METHOD FOR PREPARING POROUS COLLAGEN MATRICES

BACKGROUND OF THE INVENTION

Collagen matrices can be used to make, among others, artificial tissues, artificial organs and drug delivery vehicles. They are typically prepared by reconstituting collagen fibers extracted from connective tissues, which are rich in collagen. Conventional methods for extracting collagen fiber require rigorous physical or chemical treatment, e.g., grinding, homogenization, or acidic/basic degradation, which destroys the network structure of collagen fibers.

SUMMARY OF THE INVENTION

This invention is based on the unexpected discovery that treating a connective tissue in a mild acidic solution substantially free of salt results in swelling of the connective tissue to a great extent without disrupting the collagen network structure.

Accordingly, one aspect of this invention features a method for preparing a porous collagen matrix directly from a connective tissue. This method includes (i) providing a connective tissue having a surface ranging from 20 mm$^2$ to 2 m$^2$ (e.g., 25 mm$^2$ to 900 cm$^2$), (ii) swelling the connective tissue with an acidic solution by at least 50% (e.g., 100% to 500%) in volume to form a swollen connective tissue, and (iii) washing the swollen connective tissue to remove non-collagenous material, thereby forming a porous collagen matrix. The connective tissue can be derived from dermis or tendon. The acidic solution used for swelling the connective tissue has a pH of 1-6 (e.g., 2-4) and is substantially free of salt, i.e., a solution either having no salt or having salt at a very low concentration so that the ionic strength of the solution is not greater than 0.005 M. Examples of this acidic solution can be prepared from, among others, formic acid, oxalic acid, acetic acid, citric acid, lactic acid, malic acid, boric acid, phosphoric acid, or a mixture thereof. Preferably, it is a 0.1-6 M acetic acid solution.

Prior to the swelling step, the connective tissue can be rinsed with a solvent containing an organic solvent and optionally water. When the solvent contains both an organic solvent and water, the volume ratio of organic solvent:water can range from 1:4 to 9:1. Examples of the organic solvent include, but are not limited to, alcohol, ketone, acetone, acetonitrile, chloroform, N,N-dimethylformamide, dimethyl sulfoxide, and a mixture thereof. When the connective tissue is derived from skin and contains hairs or hair roots, it is preferably pre-treated with a proteolytic enzyme (e.g., dispase, trypsin, papain, pepsin, chymotrypsin, bromelain, ficin, and a mixture thereof) to remove the hairs or hair roots.

The swelling step can be performed by soaking the connective tissue in the acidic solution. Optionally, the soaking process is performed concurrently with squirting a liquid into the connective tissue or with ultrasound treatment.

After the swelling step, the resultant swollen connective tissue can be washed to remove non-collagenous material, thereby producing a porous collagen matrix. The washing step can be performed by soaking the swollen connective tissue in a wash solution containing a detergent, a proteolytic enzyme, or a mixture thereof. Optionally, this soaking process is carried out together with squirting a liquid into the swollen connective tissue or treating the tissue with ultrasound.

Also within the scope of this invention is a porous collagen matrix prepared by the method described above.

The details of one or more embodiments of the invention are set forth in the description below. Other features or advantages of the present invention will be apparent from the following drawings, detailed description of several examples, and also from the appended claims.

BRIEF DESCRIPTION OF THE DRAWINGS

The drawings are first described.

DETAILED DESCRIPTION OF THE INVENTION

Figure 1:
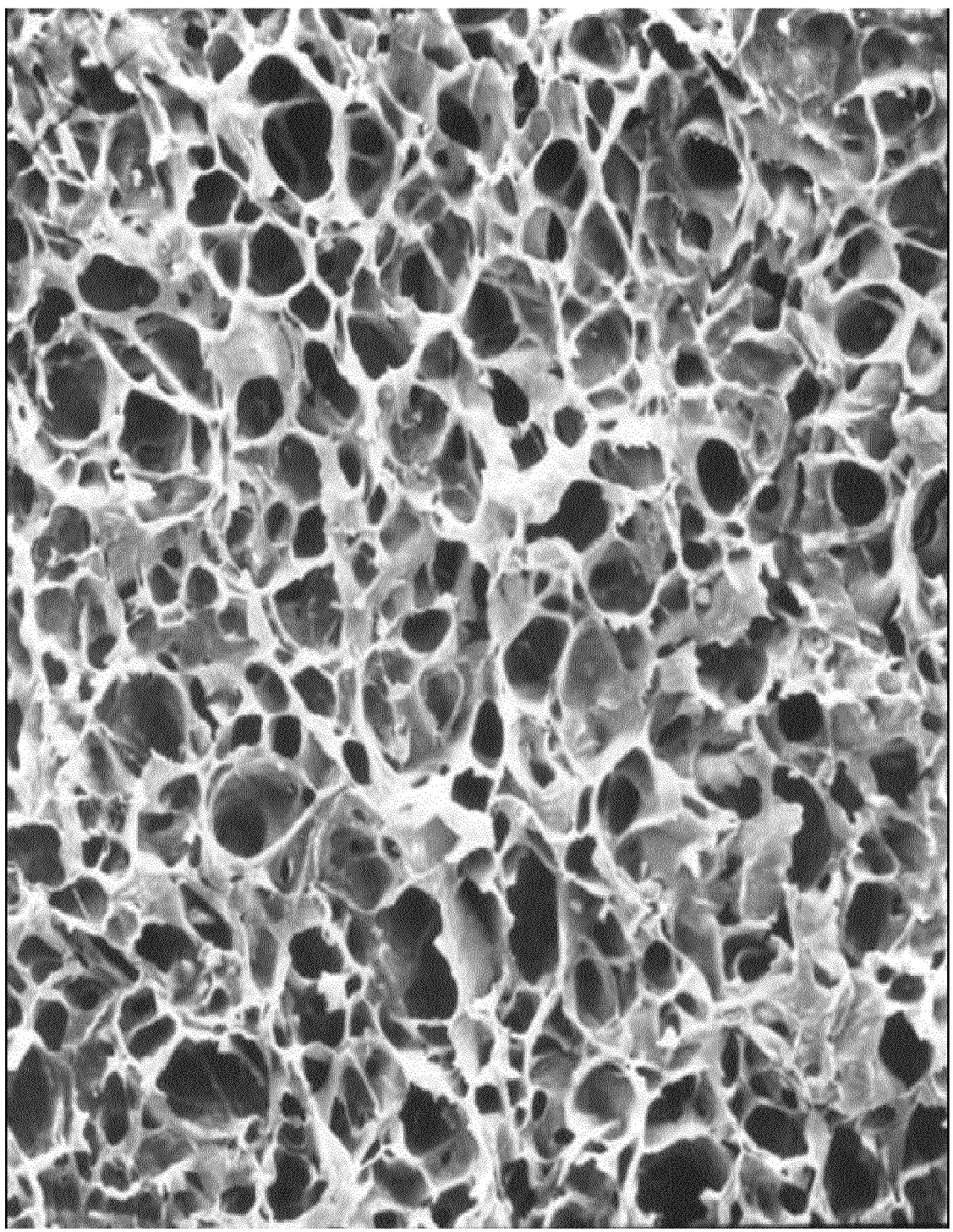
FIG. 1 is a scanning electron microscope (SEM) image of a porous collagen matrix prepared by the process described in Example 1 below (magnification: ×100)
Figure 2:
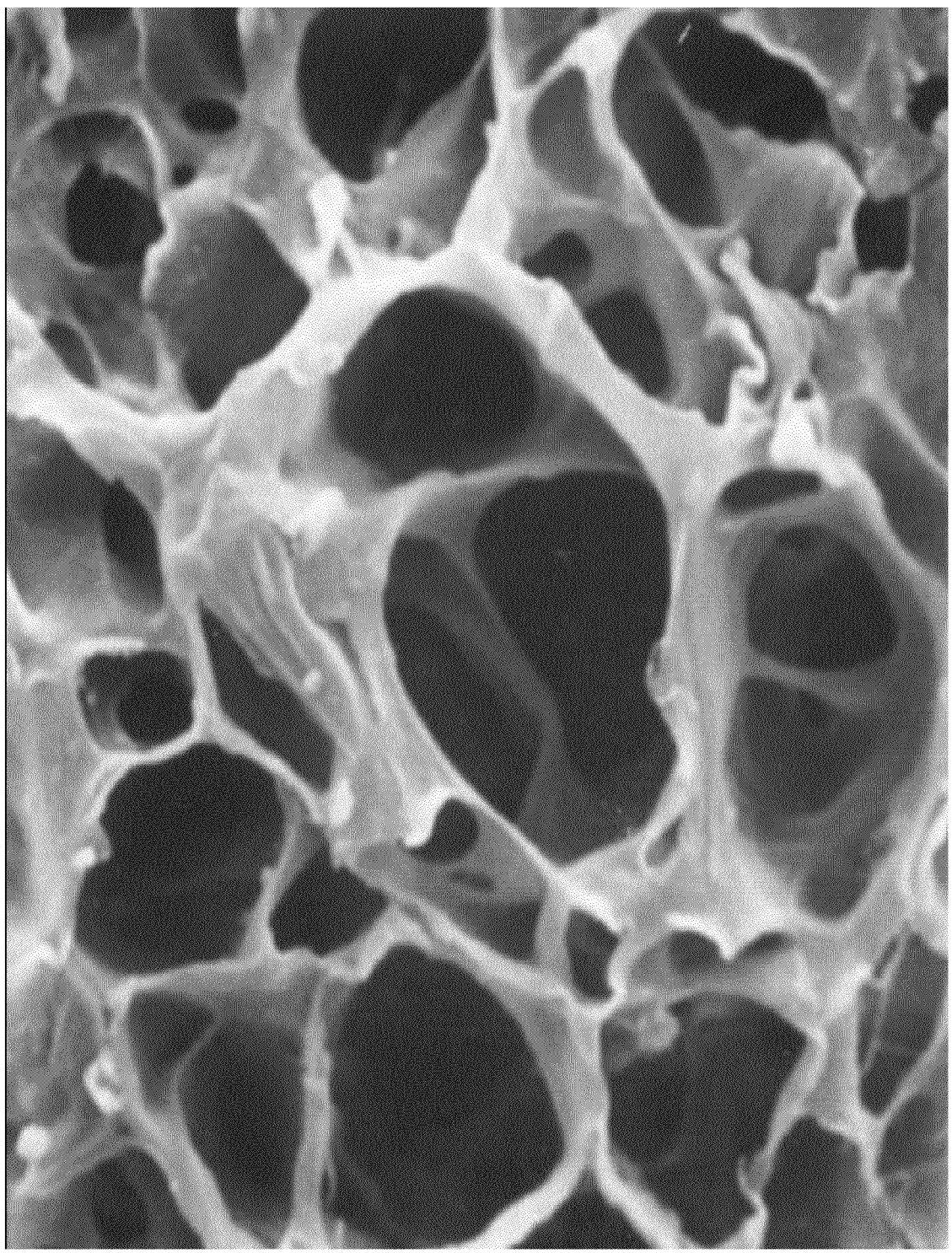
FIG. 2 is a SEM image of the porous collagen matrix prepared by the process described in Example 1 below (magnification: ×400).

Described herein is a method of preparing porous collagen matrices directly from a connective tissue, in which collagen is the major protein. Collagen is a triple-helix, rod-shaped molecule having a length of about 300 nm and a diameter of about 1.5 nm. A number of collagen molecules form a collagen fibril and a bundle of collagen fibrils form a collagen fiber. Covalent cross-linking exists inter- and intra-collagen molecules, thereby forming a fibrous network in a connective tissue.

In the method of this invention, the starting material, i.e., a connective tissue, can be derived from an animal, e.g., cattle, pig, horse, sheep, chicken, duck, turkey, goose, whale, and shark. The connective tissues suitable for use in this method include, but are not limited to, dermis, subcutaneous tissue, ligament, tendon, aponeurose, cartilage, and bone tissue. If necessary, a connective tissue is first cleaned manually (e.g., by gross dissection) or mechanically to remove undesirable materials such as fat and lipid. In one example, a dermis is obtained by removing lipid from a fresh animal skin, washing the skin with saline several times, and removing the surface layer of the animal skin with a dermatome to obtain the dermis. The dermis can be further washed with a phosphate buffered saline solution.

If desired, a connective tissue can be first treated with a suitable organic solvent or a mixture of the organic solvent and water to allow penetration of the organic solvent into the connective tissue. Examples of the organic solvents include, but not limited to, alcohol, ketone, acetone, acetonitrile, chloroform, N,N-dimethylformamide, dimethyl sulfoxide, or a mixture thereof. When a mixture of an organic solvent and water is used, the ratio between the organic solvent and water is above 1:5 (e.g., 1:4, 1:1, or 4:1).

When a connective tissue contains hairs or hair roots, it can be treated with a proteolytic enzyme (e.g., dispase, trypsin, papain, pepsin, chymotrypsin, bromelain, ficin, or a mixture thereof) that breaks down the hairs or hair roots.

Any of the connective tissues described above is then soaked in an effective amount of an acidic solution for a sufficient period to allow swelling of the connective tissue to a desired level, i.e., having a thickness of at least about 50% greater than (e.g., 2-10 times of) the original thickness. The acidic solution can be prepared from an organic acid, e.g., formic acid, oxalic acid, acetic acid, citric acid, lactic acid, malic acid, boric acid, phosphoric acid, or mixtures thereof. In one example, the acidic solution is an acetic acid solution having a concentration of 0.1 to 6 M (e.g., 0.1-2 M or 0.5-1.25 M). To achieve a better swelling effect, the acidic solution used in the present invention is substantially free of salt.

In the swelling step, the connective tissue is suspended in the acidic solution described above. If desired, a stream of liquid or a plurality of liquid streams can be applied to the connective tissue to facilitate penetration of the acidic solution into the tissue and reducing the time needed for swelling the connective tissue to a desired level. The liquid streams can be jetted out from a nozzle or an orifice installed in a container, where the connective tissue and the acidic solution are placed.

Alternatively or in addition, an ultrasonic wave, generated by a supersonic vibration device, or a high frequency water wave, generated by an electromagnetic field or a cam, can be applied to the connective tissue soaked in the acidic solution to help penetration of the acidic solution into the connective tissue.

The swollen connective tissue obtained from the swelling step described above is washed using a wash solution to remove substantially the non-collagenous material from the swollen connective tissue, thereby producing a porous collagen matrix. The wash solution can contain a detergent, a chelating agent, a proteolytic enzyme, or a mixture thereof.

Exemplary detergents for preparing the wash solution include, but are not limited to, sodium dodecyl sulphate (SDS), Tego compounds (e.g., Tween 80, Triton W. R. 1339, p-isooctylpolyoxy-ethylene phenol polymer, and Triton A20), cetylpyridinium chloride, cetyltrimethyl-ammonium bromide, dioctyl sodium sulphosuccinate, Emasol 4130 (polyoxyethylene sorbitan monoleate), Lubrol W, Nonidet P40. In one example, a wash solution containing 0.01 to 10% of SDS is used to treat the swollen connective tissue at 4 to 45° C. for 1 to 150 hours.

Chelating agents contained in the wash solution include, but are not limited to, ethylene diamine tetra-acetic acid (EDTA), 1,4,7,10-tetraazacyclododecan-e-1,4,7,10-tetraacetic acid DOTA), 1,4,7,10-tetraazacyclododecane-1,4,7,1-0-tetrakis(methylene phosphonic acid) (DOTP), trans-1,2-diaminocyclohexant-etra-acetic acid (CDTA), 4,5-dihydroxybenzene-1,3-disulphonic acid (Tiron), thiourea, 8-hydroxyquinoline-5-sulphonic acid, 3,6-disulpho-1,8-di-hydroxy-naphthalene, Eriochromeschwarz T (1-(1-hydroxy-2-naphthylazo)-2-hydroxy-5-nitro-4-naphthalene sulphonic acid), ammonium purpurate, etc. Preferably, the chelating agent is EDTA at a concentration of 0.01 to 100 mM.

Alternatively or in addition, the wash solution can contain one or more proteolytic enzyme, e.g., ficin, pepsin, trypsin, dispase, and hermolysin, for removing extracellular matrix associated proteins, other non-collagenous proteins and telopeptide of collagen molecules. Conditions used in a limited enzyme digestion, i.e., degrading non-collagenous proteins while maintaining the integrity of collagen fibers, are well known in the art.

In the washing step, the swollen connective tissue can be suspended in any of the wash solutions mentioned above for a sufficient time. In one example, a stream of liquid or a plurality of liquid streams are jetted out from a nozzle or an orifice towards the swollen tissue to facilitate removal of non-collagenous materials. The liquid stream can be a stream of water, a detergent-containing solution, or an enzyme-containing solution. In another example, the swollen tissue, soaked in the wash solution, is treated by ultrasound to improve wash efficiency.

The porous collagen matrix obtained from the washing step can be frozen slowly to allow formation of a matrix containing liquid crystals with desired sizes. It can then be lyophilized for preservation. Alternatively, it can be soaked in a phosphate buffered saline solution and stored at 4° C. When necessary, the porous collagen matrix can be crosslinked by standard chemical or physical methods. Agents for cross-linking collagen molecules include glutaraldehyde, formaldehyde, carbodiimides, and certain polyepoxy compounds (e.g., glycol diglycidyl ether, polyol polyglycidyl ether and dicarboxylic acid diglycidylester).

The above-described method for preparing collagen matrices differs from the conventional methods in at least two aspects. First, it does not require rigorous physical or chemical treatment (e.g., grinding, homogenization, or harsh acidic/basic treatment) that disrupts the fibrous collagen network in connective tissues. Second, it uses an acidic solution substantially free of salt to swell a connective tissue, while salt is commonly used in the conventional methods for stabilizing collagen fibers.

Also disclosed herein is a porous collagen matrix prepared by any of the methods described above. The porous collagen matrix can be used for preparing artificial tissues, artificial organs, implants, and drug delivery systems, or used as a scaffold for cell growth. Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Preparation of Porous Collagen Matrix from Pig Skin

The skin of a pig was harvested. After removal of lipids, the skin was washed a few times with saline. The surface layer of the skin was removed with a dermatome to obtain the dermis having a thickness of 0.3 mm. The dermis was further washed with a phosphate buffered saline. After washing, any saline residue was completely removed from the surface of the dermis.

The dermis was placed in a container filled with 0.5 M acetic acid and incubated at 37° C. for various periods to allow swelling of the dermis. During incubation, the container was placed on a shaker to allow suspension of the dermis. The thicknesses of the swollen dermis at different time points are shown in Table 1 below:

TABLE 1

Thicknesses of Swollen Dermis at Various Time Points after Acetic Acid Treatment

| | Acetic acid treating time | | | | |
|---|---|---|---|---|---|
| | 1.5 days | 2 days | 3 days | 4 days | 5 days |
| Thickness of Swollen Dermis | 0.45 mm (1.5x) | 0.6 mm (2x) | 0.9 mm (3x) | 1.2 mm (4x) | 2.4~3 mm (8x~10x) |

The swollen dermis was then soaked in a solution containing SDS (0.5%) and EDTA (0.5 mM) for 2 hours at room temperature to remove non-collagenous material and produce a porous collagen matrix.

The porous collagen matrix thus obtained was washed with an aseptic phosphate buffered saline solution to remove the residual SDS and EDTA. It was then frozen at −20° C. with a subsequent lyophilization for preservation. The lyophilized porous collagen matrix was sputtered with gold in vacuum and photographed under SEM. As shown in FIG. 1 and FIG.

2, the porous collagen matrix is free of cells and cellular debris and has a matrix structure formed by collagen fibers.

EXAMPLE 2

Preparation of Porous Collagen Matrix Using Liquid Squirting

A pig dermis was prepared and soaked in 0.5 M acetic acid following the procedures described in Example 1 above. More specifically, the dermis was immersed in the acetic acid in a container having multiple nozzles, from which a number of acetic acid streams were jetted out towards the dermis. As shown in Table 2 below, this squirting step accelerated the swelling process:

TABLE 2

Thicknesses of Swollen Dermis at Various Time Points after Acetic Acid Treatment

| | Acetic acid treating time | | |
|---|---|---|---|
| | 1 day | 1.5 days | 3 days |
| Thickness of Swollen Dermis | 0.45 mm (1.5x) | 0.9 mm (3x) | 2.4~3 mm (8x~10x) |

The swollen dermis was then washed with the SDS/EDTA solution described in Example 1 above by both soaking and squirting to produce a porous collagen matrix.

EXAMPLE 3

Preparation of Porous Collagen Matrix Using Ultrasound Treatment

A porous collagen matrix was prepared following the same procedures described in Example 2 above except that the squirting treatment was replaced with ultrasound treatment using an ultrasonic vibration device.

Results thus obtained indicate that, like squiring, the ultrasound treatment also significantly shortened the time for swelling a dermis to a suitable level.

EXAMPLE 4

Preparation of Porous Collagen Matrix from Pig Dermis Pre-Treated with Alcohol The pig dermis prepared according to Example 1 above was placed in a container filled with 30% ethanol (alcohol/water 30:70 (v/v)). The container was placed on a shaker to allow suspension of the dermis in the ethanol solution. The dermis was incubated in the 30% ethanol solution for about 14 hrs.

After the 30% ethanol solution was decanted, the container was filled with 0.5 M acetic acid and placed on a shaker to allow swelling of the dermis soaked in the acetic acid. One day later, the swollen dermis reached a thickness of 0.45 mm (1.5 times as thick as the original dermis). This indicates that ethanol pre-treatment also shortened the swelling time to obtain a 0.45 mm-thick swollen dermis.

After removing the 0.5 M acetic acid, the swollen dermis was incubated with 20% ethanol (alcohol/water 20:80 (v/v)) at room temperature for 12 hours. The porous collagen matrix thus produced was washed with deionized water and frozen at −20° C., followed by lyophilization for preservation.

EXAMPLE 5

Preparation of Porous Collagen Matrix Using Protease Treatment

A pig skin tissue was washed and then incubated in solution containing dispase (15 U/ml) for one day. The skin tissue was then subjected to swelling and washing, following the procedures described in Example 2 above to produce a porous collagen matrix. Results indicate that it took only 6 hours for the dispase-treated skin tissue to reach the thickness of 0.45 mm.

COMPARATIVE EXAMPLE 1

Conventional Method for Preparing Porous Collagen Matrix

A pig dermis was obtained according to Example 1 above and soaked in 0.5 M acetic acid at 37° C. for 12 hours with rotation. The treated dermis was then transferred to a solution containing 0.2 M acetic acid and 0.5 M NaCl and incubated for 72 hours. The dermis thus treated had a thickness of 0.36 mm (1.2 times as thick as the original thickness of dermis). Afterwards, the treated dermis was transferred to a solution containing 1% (w/v) hydrogen peroxide and incubated for 24 hours and subsequently transferred to a solution containing SDS and EDTA for further incubation at 37° C. for 24 hours. Finally, the dermis was washed with an aseptic phosphate buffered saline solution and frozen at −20° C., followed by lyophilization.

As shown above, a 0.3-mm thick dermis reached a thickness of 0.36 mm in a>72 hour period when swelled in a solution containing both acetic acid and salt (i.e., sodium chloride). Differently, as shown in Example 1, a 0.3-mm thick dermis reached a thickness of 0.9 mm in a three-day period (see Table 1 above), when swelled in a solution containing only acetic acid. This indicates that an acidic solution free of salt allows a dermis to swell at a much greater level than a solution containing both acid and salt (NaCl in this case). This may be due to the stabilization effect of the salt. More specifically, salt can stabilize collagen fibers so that they are closely packed, instead of swelling.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A process for preparing a porous collagen matrix from a connective tissue, comprising: providing a connective tissue having a surface ranging from 20 mm$^2$ to 2 m$^2$; swelling said connective tissue with an acidic solution by at least 50% in volume to form a swollen connective tissue comprising soaking said connective tissue in said acidic solution, and concurrently squirting a liquid into said connective tissue, or concurrently treating the connective tissue with ultrasound, wherein the acidic solution has a pH of 2-6 and is substantially free of salt; and washing said swollen connective tissue to remove non-collagenous material, thereby forming a porous collagen matrix 2. The process of claim 1, wherein the connective tissue has a size of 25 mm$^2$ to 900 cm$^2$.

3. The process of claim 1, wherein the acidic solution contains an acid selected from the group consisting of formic acid, carboxylic acids, oxalic acid, acetic acid, citric acid, lactic acid, malic acid, boric acid, phosphoric acid, and a mixture thereof.

4. The process of claim 3, wherein the acidic solution has a pH value of 2 to 4.

5. The process of claim 4, wherein the acidic solution contains acetic acid at a concentration of 0.1-6 M.

6. The process of claim 1, wherein in the swelling step, the connective tissue is swollen by 100%-500% in volume.

7. The process of claim 1, wherein said washing step comprises soaking said swollen connective tissue in a wash solution containing a detergent, a proteolytic enzyme, or a mixture thereof.

8. The process of claim 7, wherein said soaking step further comprises concurrently squirting a liquid into said swollen connective tissue.

9. The process of claim 7, wherein said soaking step further comprises concurrently treating the swollen connective tissue with ultrasound.

10. The process of claim 1, further comprising, prior to the swelling step, treating the connective tissue with a solvent containing an organic solvent and optionally water, wherein the organic solvent is selected from the group consisting of alcohol, ketone, acetone, acetonitrile, chloroform, N,N-dimethylformamide, dimethyl sulfoxide, and a mixture thereof.

11. The process of claim 10, wherein the solvent contains both the organic solvent and water at a volume ratio of 1:4 to 9:1.

12. The process of claim 1, wherein the connective tissue contains a plurality of hairs or hair roots, and the process further comprises, prior to the swelling step, treating the connective tissue with a proteolytic enzyme to loosen the hairs or hair roots.

13. The process of claim 12, wherein the proteolytic enzyme is selected from the group consisting of dispase, trypsin, papain, pepsin, chymotrypsin, bromelain, ficin, and a mixture thereof.

14. The process of claim 1, wherein the connective tissue is derived from dermis or tendon.

15. The process of claim 1, further comprising, after the washing step, drying the porous collagen matrix.

16. The process of claim 1, wherein the washing step is performed by treating the swollen connective tissue with a first wash solution containing a detergent, a chelating agent, or a mixture thereof, and with a second wash solution containing a proteolytic enzyme.

* * * * *